United States Patent
Woo et al.

(10) Patent No.: US 8,357,359 B2
(45) Date of Patent: Jan. 22, 2013

(54) MALODOR CONTROL COMPOSITION HAVING AN ACID CATALYST AND METHODS THEREOF

(75) Inventors: Ricky Ah-Man Woo, Hamilton, OH (US); Steven Anthony Horenziak, Cincinnati, OH (US); Rhonda Jean Jackson, Cincinnati, OH (US); Zaiyou Liu, West Chester, OH (US); Michael-Vincent Nario Malanyaon, Indian Springs, OH (US); Jason John Olchovy, West Chester, OH (US); Christine Marie Readnour, Fort Mitchell, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 146 days.

(21) Appl. No.: 12/962,691

(22) Filed: Dec. 8, 2010

(65) Prior Publication Data

US 2011/0150815 A1 Jun. 23, 2011

Related U.S. Application Data

(60) Provisional application No. 61/287,369, filed on Dec. 17, 2009.

(51) Int. Cl.
*A61L 9/00* (2006.01)
*A61L 9/01* (2006.01)
*A61K 31/33* (2006.01)

(52) U.S. Cl. .................. 424/76.2; 424/76.21; 424/76.1; 514/183

(58) Field of Classification Search .................. None
See application file for complete search history.

(56) References Cited

U.S. PATENT DOCUMENTS

| 5,089,258 | A | 2/1992 | Zaid |
| 5,942,217 | A | 8/1999 | Woo et al. |
| 5,955,093 | A | 9/1999 | Woo et al. |
| 6,033,679 | A | 3/2000 | Woo et al. |
| 7,135,449 | B2 | 11/2006 | Li et al. |
| 7,199,093 | B2 | 4/2007 | Li et al. |
| 7,393,521 | B2 | 7/2008 | Hruza |
| 7,425,526 | B2 | 9/2008 | Li et al. |
| 7,799,966 | B2 | 9/2010 | Williams et al. |
| 2004/0082928 | A1 | 4/2004 | Pesce et al. |
| 2008/0071238 | A1 | 3/2008 | Sierri et al. |

FOREIGN PATENT DOCUMENTS

| EP | 1 884 251 A1 | 2/2008 |
| EP | 2008637 A1 | 12/2008 |

OTHER PUBLICATIONS

International Search Report dated May 10, 2011 containing 105 pages.

*Primary Examiner* — Daniel Sullivan
*Assistant Examiner* — Kyle Purdy
(74) *Attorney, Agent, or Firm* — Amy I Ahn-Roll

(57) ABSTRACT

A malodor control composition having at least one volatile aldehyde and an acid catalyst, and methods thereof are provided. The malodor control composition is suitable for a variety of applications, including use in fabric and air freshening products.

14 Claims, 3 Drawing Sheets

MALODOR CONTROL COMPOSITION HAVING AN ACID CATALYST AND METHODS THEREOF

CROSS-REFERENCES TO RELATED APPLICATIONS

This application claims priority to U.S. Provisional Application Ser. No. 61/287,369 filed Dec. 17, 2009.

FIELD OF THE INVENTION

The present invention relates to a malodor control composition having at least one volatile aldehyde and an acid catalyst, and methods thereof. The malodor control composition is suitable for use in a variety of applications, including use in fabric and air freshening products.

BACKGROUND OF THE INVENTION

Products for reducing or masking malodors are well known in the art and are widely described in patent literature. These products may be designed to work specifically in air or on fabrics or other surfaces. See, e.g., U.S. Pat. Nos. 5,942,217; 5,955,093; and 6,033,679. However, not all odors are effectively controlled by products on the market as amine-based malodors such as fish and urine malodors, and sulfur-based malodors such as garlic, onion, foot, and fecal malodors are difficult to combat. Further, the time required for a composition to noticeably combat malodors may create consumer doubt as to a product's efficacy on malodors. For example, the consumer may leave the treated space before the product begins to noticeably reduce the malodor.

The difficulty in overcoming a broad range of malodors has spawned a diverse assortment of products to neutralize, mask, or contain the malodors. There remains a need for a fast acting malodor control composition that neutralizes malodors and is effective on a broad range of malodors, including amine-based and sulfur-based malodors, while not overpowering malodors with an overwhelming perfume.

SUMMARY OF THE INVENTION

In one embodiment, the malodor control composition comprises at least one volatile aldehyde; an acid catalyst having a vapor pressure of about 0.01 to about 13 at 25° C.

In another embodiment, there is provided a method of neutralizing malodor comprising contacting a malodor with a malodor control composition comprising at least one volatile aldehyde; an acid catalyst having a vapor pressure of about 0.01 to about 13 at 25° C.

DETAILED DESCRIPTION OF THE INVENTION

Figure 1:
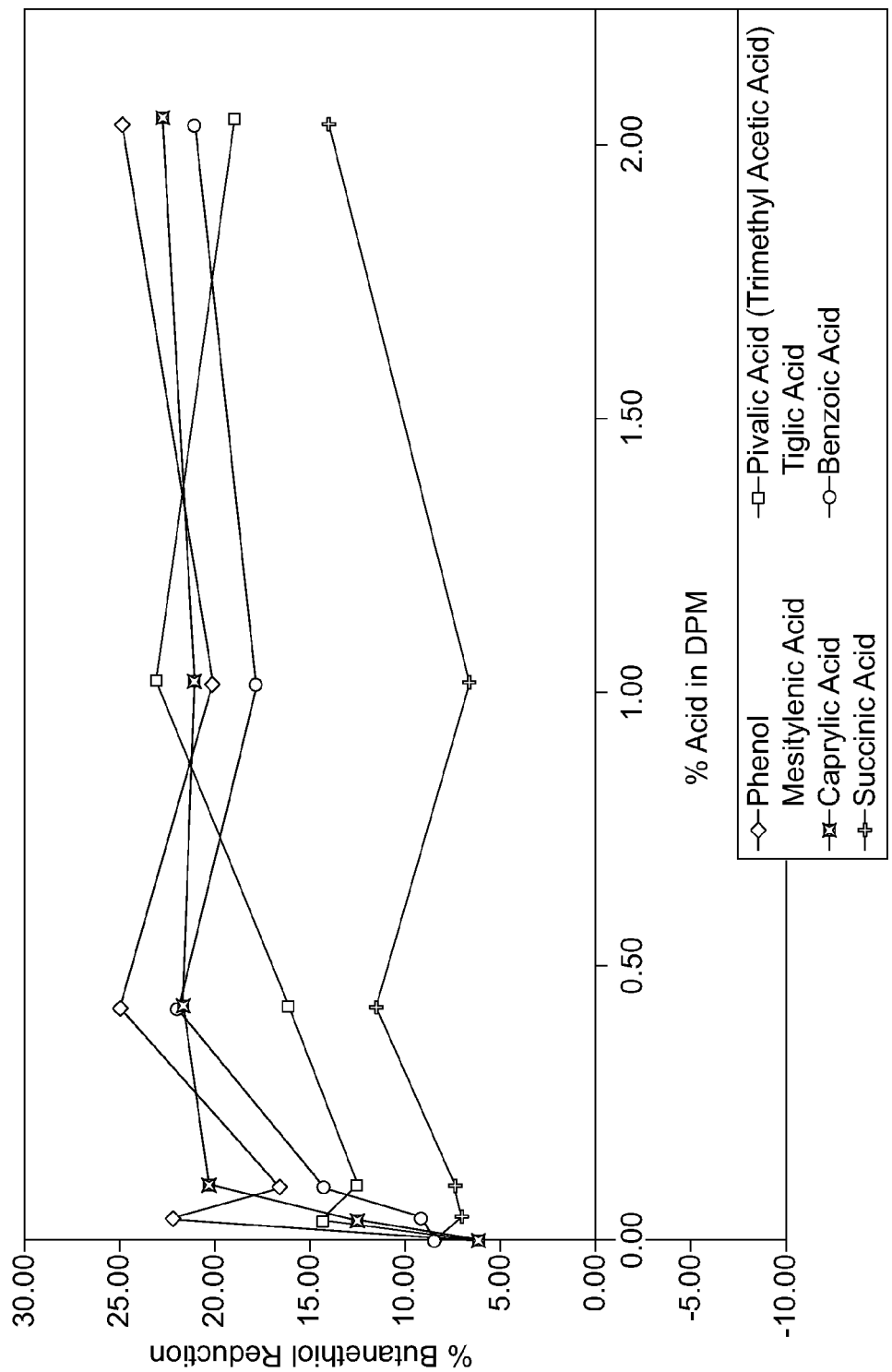
FIG. 1 is a graph showing butanethiol reduction by thiophene carboxaldehyde in combination with various acid catalysts.

The present invention relates to a malodor control composition having at least one volatile aldehyde and an acid catalyst for neutralizing malodors, and methods thereof.

"Malodor" refers to compounds generally offensive or unpleasant to most people, such as the complex odors associated with bowel movements.

"Neutralize" or "neutralization" refers to the ability of a compound or product to reduce or eliminate malodorous compounds. Odor neutralization may be partial, affecting only some of the malodorous compounds in a given context, or affecting only part of a malodorous compound. A malodorous compound may be neutralized by chemical reaction resulting in a new chemical entity, by sequestration, by chelation, by association, or by any other interaction rendering the malodorous compound less malodorous or non-malodorous. Odor neutralization may be distinguished from odor masking or odor blocking by a change in the malodorous compound, as opposed to a change in the ability to perceive the malodor without any corresponding change in the condition of the malodorous compound.

I. Malodor Control Composition

The malodor control composition includes a mixture of volatile aldehydes and is designed to deliver genuine malodor neutralization and not function merely by covering up or masking odors. A genuine malodor neutralization provides a sensory and analytically measurable (e.g. gas chromatograph) malodor reduction. Thus, if the malodor control composition delivers a genuine malodor neutralization, the composition will reduce malodors in the vapor and/or liquid phase.

1. Volatile Aldehydes

The malodor control composition includes a mixture of volatile aldehydes that neutralize malodors in vapor and/or liquid phase via chemical reactions. Such volatile aldehydes are also called reactive aldehydes (RA). Volatile aldehydes may react with amine-based odors, following the path of Schiff-base formation. Volatiles aldehydes may also react with sulfur-based odors, forming thiol acetals, hemi thiolacetals, and thiol esters in vapor and/or liquid phase. It may be desirable for these vapor and/or liquid phase volatile aldehydes to have virtually no negative impact on the desired perfume character of a product. Aldehydes that are partially volatile may be considered a volatile aldehyde as used herein.

Suitable volatile aldehydes may have a vapor pressure (VP) in the range of about 0.0001 torr to 100 torr, alternatively about 0.0001 torr to about 10 torr, alternatively about 0.001 torr to about 50 torr, alternatively about 0.001 torr to about 20 torr, alternatively about 0.001 torr to about 0.100 torr, alternatively about 0.001 torr to 0.06 torr, alternatively about 0.001 torr to 0.03 torr, alternatively about 0.005 torr to about 20 torr, alternatively about 0.01 torr to about 20 torr, alternatively about 0.01 torr to about 15 torr, alternatively about 0.01 torr to about 10 torr, alternatively about 0.05 torr to about 10 torr, measured at 25° C.

The volatile aldehydes may also have a certain boiling point (B.P.) and octanol/water partition coefficient (P). The boiling point referred to herein is measured under normal standard pressure of 760 mmHg. The boiling points of many volatile aldehydes, at standard 760 mm Hg are given in, for example, "Perfume and Flavor Chemicals (Aroma Chemicals)," written and published by Steffen Arctander, 1969.

The octanol/water partition coefficient of a volatile aldehyde is the ratio between its equilibrium concentrations in octanol and in water. The partition coefficients of the volatile aldehydes used in the malodor control composition may be more conveniently given in the form of their logarithm to the base 10, log P. The log P values of many volatile aldehydes have been reported. See, e.g., the Pomona92 database, available from Daylight Chemical Information Systems, Inc. (Daylight CIS), Irvine, Calif. However, the log P values are most conveniently calculated by the "C LOG P" program, also available from Daylight CIS. This program also lists experimental log P values when they are available in the Pomona92 database. The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each volatile aldehyde, and takes into account the numbers and types of atoms, the atom connectivity, and chemical bonding. The C log P values, which are the most reliable and widely used estimates for this physicochemical property, are preferably used instead of the experimental log P values in the selection of volatile aldehydes for the malodor control composition.

The C log P values may be defined by four groups and the volatile aldehydes may be selected from one or more of these groups. The first group comprises volatile aldehydes that have a B.P. of about 250° C. or less and C log P of about 3 or less. The second group comprises volatile aldehydes that have a B.P. of 250° C. or less and C log P of 3.0 or more. The third group comprises volatile aldehydes that have a B.P. of 250° C. or more and C log P of 3.0 or less. The fourth group comprises volatile aldehydes that have a B.P. of 250° C. or more and C log P of 3.0 or more. The malodor control composition may comprise any combination of volatile aldehydes from one or more of the C log P groups.

In some embodiments, the malodor control composition of the present invention may comprise, by total weight of the malodor control composition, from about 0% to about 30% of volatile aldehydes from group 1, alternatively about 25%; and/or about 0% to about 10% of volatile aldehydes from group 2, alternatively about 10%; and/or from about 10% to about 30% of volatile aldehydes from group 3, alternatively about 30%; and/or from about 35% to about 60% of volatile aldehydes from group 4, alternatively about 35%.

Exemplary volatile aldehydes which may be used in a malodor control composition include, but are not limited to, Adoxal (2,6,10-Trimethyl-9-undecenal), Bourgeonal (4-t-butylbenzenepropionaldehyde), Lilestralis 33 (2-methyl-4-t-butylphenyl)propanal), Cinnamic aldehyde, cinnamaldehyde (phenyl propenal, 3-phenyl-2-propenal), Citral, Geranial, Neral (dimethyloctadienal, 3,7-dimethyl-2,6-octadien-1-al), Cyclal C (2,4-dimethyl-3-cyclohexen-1-carbaldehyde), Florhydral (3-(3-Isopropyl-phenyl)-butyraldehyde), Citronellal (3,7-dimethyl 6-octenal), Cymal, cyclamen aldehyde, Cyclosal, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyl octan-1-al), Helional (alpha-methyl-3,4-(methylenedioxy)-hydrocinnamaldehyde, hydrocinnamaldehyde (3-phenylpropanal, 3-phenylpropionaldehyde), Intreleven aldehyde (undec-10-en-1-al), Ligustral, Trivertal (2,4-dimethyl-3-cyclohexene-1-carboxaldehyde), Jasmorange, satinaldehyde (2-methyl-3-tolylpropionaldehyde, 4-dimethylbenzenepropanal), Lyral (4-(4-hydroxy-4-methyl pentyl)-3-cyclohexene-1-carboxaldehyde), Melonal (2,6-Dimethyl-5-Heptenal), Methoxy Melonal (6-methoxy-2,6-dimethylheptanal), methoxycinnamaldehyde (trans-4-methoxycinnamaldehyde), Myrac aldehyde isohexenyl cyclohexenyl-carboxaldehyde, trifernal ((3-methyl-4-phenyl propanal, 3-phenyl butanal), lilial, P.T. Bucinal, lysmeral, benzenepropanal (4-tert-butyl-alpha-methyl-hydrocinnamaldehyde), Dupical, tricyclodecylidenebutanal (4-Tricyclo5210-2,6decylidene-8butanal), Melafleur (1,2,3,4,5,6,7,8-octahydro-8,8-dimethyl-2-naphthaldehyde), Methyl Octyl Acetaldehyde, aldehyde C-11 MOA (2-methyl deca-1-al), Onicidal (2,6,10-trimethyl-5,9-undecadien-1-al), Citronellyl oxyacetaldehyde, Muguet aldehyde 50 (3,7-dimethyl-6-octenyl) oxyacetaldehyde), phenylacetaldehyde, Mefranal (3-methyl-5-phenyl pentanal), Triplal, Vertocitral dimethyl tetrahydrobenzene aldehyde (2,4-dimethyl-3-cyclohexene-1-carboxaldehyde), 2-phenylpropionaldehyde, Hydrotropaldehyde, Canthoxal, anisylpropanal 4-methoxy-alpha-methyl benzenepropanal (2-anisylidene propanal), Cylcemone A (1,2,3,4,5,6,7,8-octahydro-8,8-dimethyl-2-naphthaldehyde), and Precylcemone B (1-cyclohexene-1-carboxaldehyde).

Still other exemplary aldehydes include, but are not limited to, acetaldehyde (ethanal), pentanal, valeraldehyde, amylaldehyde, Scentenal (octahydro-5-methoxy-4,7-Methano-1H-indene-2-carboxaldehyde), propionaldehyde (propanal), Cyclocitral, beta-cyclocitral, (2,6,6-trimethyl-1-cyclohexene-1-acetaldehyde), Iso Cyclocitral (2,4,6-trimethyl-3-cyclohexene-1-carboxaldehyde), isobutyraldehyde, butyraldehyde, isovaleraldehyde (3-methyl butyraldehyde), methylbutyraldehyde (2-methyl butyraldehyde, 2-methyl butanal), Dihydrocitronellal (3,7-dimethyl octan-1-al), 2-Ethylbutyraldehyde, 3-Methyl-2-butenal, 2-Methylpentanal, 2-Methyl Valeraldehyde, Hexenal (2-hexenal, trans-2-hexenal), Heptanal, Octanal, Nonanal, Decanal, Lauric aldehyde, Tridecanal, 2-Dodecanal, Methylthiobutanal, Glutaraldehyde, Pentanedial, Glutaric aldehyde, Heptenal, cis or trans-Heptenal, Undecenal (2-, 10-), 2,4-octadienal, Nonenal (2-, 6-), Decenal (2-, 4-), 2,4-hexadienal, 2,4-Decadienal, 2,6-Nonadienal, Octenal, 2,6-dimethyl 5-heptenal, 2-isopropyl-5-methyl-2-hexenal, Trifernal, beta methyl Benzenepropanal, 2,6,6-Trimethyl-1-cyclohexene-1-acetaldehyde, phenyl Butenal (2-phenyl2-butenal), 2.Methyl-3(p-isopropylphenyl)-propionaldehyde, 3-(p-isopropylphenyl)-propionaldehyde, p-Tolylacetaldehyde (4-methylphenylacetaldehyde), Anisaldehyde (p-methoxybenzene aldehyde), Benzaldehyde, Vernaldehyde (1-Methyl-4-(4-methylpentyl)-3-cyclohexenecarbaldehyde), Heliotropin (piperonal) 3,4-Methylene dioxy benzaldehyde, alpha-Amylcinnamic aldehyde, 2-pentyl-3-phenylpropanoic aldehyde, Vanillin (4-methoxy 3-hydroxy benzaldehyde), Ethyl vanillin (3-ethoxy 4-hydroxybenzaldehyde), Hexyl Cinnamic aldehyde, Jasmonal H (alpha-n-hexyl-cinnamaldehyde), Floralozone, (para-ethyl-alpha,alpha-dimethyl Hydrocinnamaldehyde), Acalea (p-methyl-alpha-pentylcinnamaldehyde), methylcinnamaldehyde, alpha-Methylcinnamaldehyde (2-methyl 3-phenyl propenal), alpha-hexylcinnamaldehyde (2-hexyl 3-phenyl propenal), Salicylaldehyde (2-hydroxy benzaldehyde), 4-ethyl benzaldehyde, Cuminaldehyde (4-isopropyl benzaldehyde), Ethoxybenzaldehyde, 2,4-dimethylbenzaldehyde, Veratraldehyde (3,4-dimethoxybenzaldehyde), Syringaldehyde (3,5-dimethoxy 4-hydroxybenzaldehyde), Catechaldehyde (3,4-dihydroxybenzaldehyde), Safranal (2,6,6-trimethyl-1,3-diene methanal), Myrtenal (pin-2-ene-1-carbaldehyde), Perillaldehyde L-4 (1-methylethenyl)-1-cyclohexene-1-carboxaldehyde), 2,4-Dimethyl-3-cyclohexene carboxaldehyde, 2-Methyl-2-pentenal, 2-methylpentenal, pyruvaldehyde, formyl Tricyclodecan, Mandarin aldehyde, Cyclemax, Pino acetaldehyde, Corps Iris, Maceal, and Corps 4322.

In one embodiment, the malodor control composition includes a mixture of two or more volatile aldehydes selected from the group consisting of 2-ethoxy Benzylaldehyde, 2-isopropyl-5-methyl-2-hexenal, 5-methyl Furfural, 5-methyl-thiophene-carboxaldehyde, Adoxal, p-anisaldehyde, Benzylaldehyde, Bourgenal, Cinnamic aldehyde, Cymal, Decyl aldehyde, Floral super, Florhydral, Helional, Lauric aldehyde, Ligustral, Lyral, Melonal, o-anisaldehyde, Pino acetaldehyde, P.T. Bucinal, Thiophene carboxaldehyde, trans-4-Decenal, trans trans 2,4-Nonadienal, Undecyl aldehyde, and mixtures thereof.

In some embodiments, the malodor control composition includes fast reacting volatile aldehydes. "Fast reacting volatile aldehydes" refers to volatile aldehydes that either (1) reduce amine odors by 20% or more in less than 40 seconds; or (2) reduce thiol odors by 20% or more in less than 30 minutes.

In one embodiment, the malodor control composition includes a mixture of the volatile aldehydes listed in Table 1 and referred to herein as Accord A.

TABLE 1

Accord A

| Material | Wt. % | CAS Number | ClogP Group | VP(torr) @25° C. |
|---|---|---|---|---|
| Intreleven Aldehyde | 5.000 | 112-45-8 | 3 | 0.060 |
| Florhydral | 10.000 | 125109-85-5 | 4 | 0.008 |
| Floral Super | 25.000 | 71077-31-1 | 3 | 0.030 |
| Scentenal | 10.000 | 86803-90-9 | 2 | 0.010 |
| Cymal | 25.000 | 103-95-7 | 4 | 0.007 |
| o-anisaldehyde | 25.000 | 135-02-4 | 1 | 0.032 |

In another embodiment, the malodor control composition includes a mixture of the volatile aldehydes listed in Table 2 and referred to herein as Accord B.

TABLE 2

Accord B

| Material | Wt. % | CAS Number | ClogP Group | VP (torr) @25° C. |
|---|---|---|---|---|
| Intreleven Aldehyde | 2.000 | 112-45-8 | 3 | 0.060 |
| Florhydral | 20.000 | 125109-85-5 | 4 | 0.008 |
| Floral Super | 10.000 | 71077-31-1 | 3 | 0.030 |
| Scentenal | 5.000 | 86803-90-9 | 2 | 0.010 |
| Cymal | 25.000 | 103-95-7 | 4 | 0.007 |
| Floralozone | 10.000 | 67634-14-4 | 4 | 0.005 |
| Adoxal | 1.000 | 141-13-9 | 4 | 0.007 |
| Methyl Nonyl Acetaldehyde | 1.000 | 110-41-8 | 3 | 0.030 |
| Melonal | 1.000 | 106-72-9 | 3 | 0.670 |
| o-anisaldehyde | 25.000 | 135-02-4 | 1 | 0.032 |

In another embodiment, the malodor control composition includes a mixture of about 71.2% volatile aldehydes, the remainder being other an ester and an alcohol perfume raw material. This mixture is listed in Table 3 and referred to herein as Accord C.

TABLE 3

Accord C

| Material | Wt. % | CAS Number | ClogP Group | VP (torr) @25° C. |
|---|---|---|---|---|
| Intreleven Aldehyde | 2.000 | 112-45-8 | 3 | 0.060 |
| Florhydral | 10.000 | 125109-85-5 | 4 | 0.008 |
| Floral Super | 5.000 | 71077-31-1 | 3 | 0.030 |
| Scentenal | 2.000 | 86803-90-9 | 2 | 0.010 |
| Cymal | 15.000 | 103-95-7 | 4 | 0.007 |
| Floralozone | 12.000 | 67634-14-4 | 4 | 0.005 |
| Adoxal | 1.000 | 141-13-9 | 4 | 0.007 |
| Methyl Nonyl Acetaldehyde | 1.000 | 110-41-8 | 3 | 0.030 |
| Melonal | 1.000 | 106-72-9 | 3 | 0.670 |
| Flor Acetate | 11.800 | 5413-60-5 | 1 | 0.060 |

TABLE 3-continued

Accord C

| Material | Wt. % | CAS Number | ClogP Group | VP (torr) @25° C. |
|---|---|---|---|---|
| Frutene | 7.000 | 17511-60-3 | 4 | 0.020 |
| Helional | 5.000 | 1205-17-0 | 2 | 0.0005 |
| Bourgeonal | 2.000 | 18127-01-0 | 4 | 0.004 |
| Linalool | 10.000 | 78-70-6 | 3 | 0.050 |
| Benzaldehyde | 0.200 | 100-52-7 | 1 | 1.110 |
| o-anisaldehyde | 15.000 | 135-02-4 | 1 | 0.320 |

Accords A, B, or C can be formulated in with other perfume raw materials in an amount, for example, of about 10% by weight of the malodor control composition. Additionally, the individual volatile aldehydes or a various combination of the volatile aldehydes can be formulated into a malodor control composition. In certain embodiments, the volatile aldehydes may be present in an amount up to 100%, by weight of the malodor control composition, alternatively from 1% to about 100%, alternatively from about 2% to about 100%, alternatively from about 3% to about 100%, alternatively about 50% to about 100%, alternatively about 70% to about 100%, alternatively about 80% to about 100%, alternatively from about 1% to about 20%, alternatively from about 1% to about 10%, alternatively from about 1% to about 5%, alternatively from about 1% to about 3%, alternatively from about 2% to about 20%, alternatively from about 3% to about 20%, alternatively from about 4% to about 20%, alternatively from about 5% to about 20%, by weight of the composition.

In some embodiments where volatility is not important for neutralizing a malodor, the present invention may include poly-aldehydes, for example, di-, tri-, tetra-aldehydes. Such embodiments may include laundry detergents, additive, and the like for leave-on, through the wash, and rinse-off type of applications.

2. Acid Catalyst

The malodor control composition of the present invention may include an effective amount of an acid catalyst to neutralize sulfur-based malodors. It has been found that certain mild acids have an impact on aldehyde reactivity with thiols in the liquid and vapor phase. It has been found that the reaction between thiol and aldehyde is a catalytic reaction that follows the mechanism of hemiacetal and acetal formation path. When the present malodor control composition contains an acid catalyst and contacts a sulfur-based malodor, the volatile aldehyde reacts with thiol. This reaction may form a thiol acetal compound, thus, neutralizing the sulfur-based odor. Without an acid catalyst, only hemi-thiol acetal is formed.

Suitable acid catalysts have a VP, as reported by Scifinder, in the range of about 0.001 torr to about 38 torr, measured at 25° C., alternatively about 0.001 torr to about 14 torr, alternatively from about 0.001 to about 1, alternatively from about 0.001 to about 0.020, alternatively about 0.005 to about 0.020, alternatively about 0.010 to about 0.020.

The acid catalyst may be a weak acid. A weak acid is characterized by an acid dissociation constant, $K_a$, which is an equilibrium constant for the dissociation of a weak acid; the pKa being equal to minus the decimal logarithm of $K_a$. The acid catalyst may have a pKa from about 4.0 to about 6.0, alternatively from about 4.3 and 5.7, alternatively from about 4.5 to about 5, alternatively from about 4.7 to about 4.9. Suitable acid catalyst include those listed in Table 4.

TABLE 4

| Material | VP (torr) @ 25° C. |
|---|---|
| Formic Acid | 36.5 |
| Acetic Acid | 13.9 |
| Trimethyl Acetic Acid | 0.907 |
| Phenol (alkaline in liquid apps yet acidic in vapor phase) | 0.610 |
| Tiglic acid | 0.152 |
| Caprylic acid | 0.0222 |
| 5-Methyl thiophene carboxylic acid | 0.019 |
| Succinic acid | 0.0165 |
| Benzoic acid | 0.014 |
| Mesitylenic acid | 0.00211 |

Depending on the desired use of the malodor control composition, one may consider the scent character or the affect on the scent of the malodor control composition when selecting an acid catalyst. In some embodiments of the malodor control composition, it may be desirable to select an acid catalyst that provides a neutral to pleasant scent. Such acid catalysts may have a VP of about 0.001 torr to about 0.020 torr, measured at 25° C., alternatively about 0.005 torr to about 0.020 torr, alternatively about 0.010 torr to about 0.020 torr. Non-limiting examples of such acid catalyst include 5-methyl thiophene carboxaldehyde with carboxylic acid impurity, succinic acid, or benzoic acid.

The malodor control composition may include about 0.05% to about 5%, alternatively about 0.1% to about 1.0%, alternatively about 0.1% to about 0.5%, alternatively about 0.1% to about 0.4%, alternatively about 0.4% to about 1.5%, alternatively about 0.4% of an acid catalyst by weight of the malodor control composition.

In an acetic acid system, the present malodor control composition may include about 0.4% of acetic acid (50:50 TC:DPM, 0.4% acetic acid).

TABLE 5

| Sample Formulated | Actual % acetic acid in DPM | % butanethiol reduction @ 30 min. |
|---|---|---|
| 50:50 TC:DPM 0% Acetic Acid | 0.00 | 12.00 |
| 50:50 TC:DPM 0.05% Acetic Acid | 0.04 | 14.65 |
| 50:50 TC:DPM 0.1% Acetic Acid | 0.10 | 25.66 |
| 50:50 TC:DPM 0.2% Acetic Acid | 0.42 | 34.68 |
| 50:50 TC:DPM 0.5% Acetic Acid | 1.00 | 24.79 |
| 50:50 TC:DPM 1.0% Acetic Acid | 2.00 | 7.26 |

When an acid catalyst is present with a volatile aldehyde (or RA), the acid catalyst may increase the efficacy of the volatile aldehyde on malodors in comparison to the malodor efficacy of the volatile aldehyde on its own. For example, 1% volatile aldehyde and 1.5% benzoic acid provides malodor removal benefit equal to or better than 5% volatile aldehyde alone.

The malodor control composition may have a pH from about 3 to about 8, alternatively from about 4 to about 7, alternatively from about, alternatively from about 4 to about 6.

3. Optional Ingredients

The malodor control composition may, optionally, include odor masking agents, odor blocking agents, and/or diluents. For example, the malodor control composition may include a mixture of volatile aldehydes for neutralizing a malodor, perfume inones, and a diluent. Alternatively, the malodor control composition may include 100% volatile aldehydes.

"Odor-masking agents" refer to known compounds (e.g. perfume raw materials) that mask or hide a malodorous compound. Odor-masking may include a compound with a non-offensive or pleasant smell that is dosed such it limits the ability to sense a malodorous compound. Odor-masking may involve the selection of compounds which coordinate with an anticipated malodor to change the perception of the overall scent provided by the combination of odorous compounds.

"Odor blocking agents" refer to known compounds that dull the human sense of smell.

Exemplary diluents include dipropylene glycol methyl ether, and 3-methoxy-3-methyl-1-butanol, and mixtures thereof.

The malodor control composition may also, optionally, include perfume raw materials that solely provide a hedonic benefit (i.e. that do not neutralize malodors yet provide a pleasant fragrance). Suitable perfumes are disclosed in U.S. Pat. No. 6,248,135, which is incorporated in its entirety by reference.

II. Methods of Use

The malodor control composition of the present invention may be used in a wide variety of applications that neutralize malodors in the vapor and/or liquid phase. In some embodiments, the malodor control composition may be formulated for use in energized vapor phase systems. "Energized" as used herein refers to a system that operates by using an electrical energy source, such as a battery or electrical wall outlet, to emit a targeted active. For such systems, the VP of the volatile aldehydes may be about 0.001 torr to about 20 torr, alternatively about 0.01 torr to about 10 torr, measured at 25° C. One example of an energized vapor phase system is a liquid electric plug-in type air freshening device.

In some embodiments, the malodor control composition may be formulated for use in non-energized vapor phase systems. "Non-energized" as used herein refers to a system that emits a targeted active passively or without the need for an electrical energy source. Aerosol sprayers and traditional trigger/pump sprayers are considered non-energized systems. For such non-energized systems, the VP of the volatile aldehydes may be about 0.01 torr to about 20 torr, alternatively about 0.05 torr to about 10 torr, measured at 25° C. Non-limiting examples of a non-energized vapor phase system are passive air freshening diffusers such as those known by the trade name Renuzit® Crystal Elements; and aerosol sprays such as fabric and air freshening sprays and body deodorants.

In other embodiments, the malodor control composition may be formulated for use in a liquid phase system. For such systems, the VP may be about 0 torr to about 20 torr, alternatively about 0.0001 torr to about 10 torr, measured at 25° C. Non-limiting examples of a liquid phase system are liquid laundry products, such as laundry detergents and additives; dish detergents; personal hygiene products such as body washes, shampoos, conditioners.

The malodor control composition may also be formulated for use in substrates such as plastics, wovens, or non-wovens (e.g cellulose fibers for paper products). Such substrates may be used as pet food packaging; paper towels; tissues; trash bags; diapers; baby wipes; adult incontinence products; feminine hygiene products such as sanitary napkins and tampons. The malodor control composition may also be formulated for use in commercial or industrial systems such as in septic tanks or sewage treatment equipment.

EXAMPLES

Analytical Test—Effect of Volatile Aldehydes on Amine-Based and Sulfur-Based Malodors Malodor standards are prepared by pipetting 1 mL of butylamine (amine-based malodor) and butanethiol (sulfur-based malodor) into a 1.2 liter gas sampling bag. The bag is then filled to volume with nitrogen and allowed to sit for at least 12 hours to equilibrate.

A 1 µL sample of each volatile aldehyde listed in Table 6 and of each Accord (A, B, and C) listed in Tables 1 to 3 is pipetted into individual 10 mL silanized headspace vials. The vials are sealed and allowed to equilibrate for at least 12 hours. Repeat 4 times for each sample (2 for butylamine analysis and 2 for butanethiol analysis).

After the equilibration period, 1.5 mL of the target malodor standard is injected into each 10 mL vial. For thiol analysis, the vials containing a sample+malodor standard are held at room temperature for 30 minutes. Then, a 1 mL headspace syringe is then used to inject 250 µL of each sample/malodor into a GC/MS split/splitless inlet. For amine analysis, a 1 mL headspace syringe is used to inject 500 µL of each sample/malodor immediately into the GC/MS split/splitless inlet. A GC pillow is used for the amine analysis to shorten the run times.

Samples are then analyzed using a GC/MS with a DB-5, 20 m, 1 µm film thickness column with an MPS-2 autosampler equipment with static headspace function. Data is analyzed by ion extraction on each total ion current (56 for thiol and 30 for amine) and the area is used to calculate the percent reduction from the malodor standard for each sample.

Table 6 shows the effect of certain volatile aldehydes on neutralizing amine-based and sulfur based malodors at 40 seconds and 30 minutes, respectively.

TABLE 6

| Perfume Raw Material (R—CHO) | At least 20% butylamine reduction at 40 secs.? | At least 20% butanethiol reduction at 30 mins.? |
|---|---|---|
| 2,4,5 Trimethoxy Benzaldehyde | No | No |
| 2,4,6-Trimethoxy-benzylaldehyde | No | No |
| 2-ethoxy benzylaldehyde | Yes | Yes |
| 2-isopropyl-5-methyl-2-hexenal | Yes | Yes |
| 2-methyl-3-(2-furyl)-propenal | No | No |
| 3,4,5 Trimethoxy Benzaldehyde | No | No |
| 3,4-Trimethoxy-benzylaldehyde | No | No |
| 4-tertbutyl benzylaldehyde | Yes | No |
| 5-methyl furfural | Yes | Yes |
| 5-methyl-thiophene-carboxaldehyde | No | Yes |
| Adoxal | Yes | No |
| Amyl cinnamic aldehyde | No | No |
| Benzylaldehyde | Yes | No |
| Bourgenal | No | Yes |
| Cinnamic aldehyde | Yes | Yes |
| Citronelyl Oxyacetaldehyde | No | No |
| Cymal | Yes | No |
| Decyl aldehyde | Yes | No |
| Floral Super | Yes | Yes |
| Florhydral | Yes | Yes |
| Floralozone | No | No |
| Helional | Yes | No |
| Hydroxycitronellal | No | No |
| Lauric aldehyde | Yes | No |
| Ligustral | Yes | No |
| Lyral | Yes | No |
| Melonal | Yes | No |
| Methyl nonyl acetaldehyde | No | No |
| o-anisaldehyde | Yes | Yes |
| p-anisaldehyde | Yes | No |
| Pino acetaldehyde | Yes | Yes |
| P.T. Bucinal | Yes | No |
| Thiophene Carboxaldehyde | Yes | No |
| Trans-4-decenal | Yes | Yes |
| Trans Trans 2,4-Nonadienal | Yes | No |
| Undecyl aldehyde | Yes | No |

Table 7 shows the percent reduction of butylamine and butanethiol at 40 seconds and 30 minutes, respectively, for Accords A, B, and C.

TABLE 7

| Accord | % reduction of butylamine at 40 secs. | % reduction of butanethiol at 30 mins. |
|---|---|---|
| Accord A | 76.58 | 25.22 |
| Accord B | 51.54 | 35.38 |
| Accord C | 65.34 | 24.98 |

Analytical Test—Effect of Acid Catalysts on Sulfur-Based Malodors

The above analytical test is repeated using samples containing an acid catalyst to test their effect on sulfur-based malodors. Specifically, a 1 µL aliquot of each of the following controls and acid catalyst samples are pipetted into individual 10 mL silanized headspace vials in duplicate: thiophene carboxyaldehyde as a control; a 50/50 mixture of thiophene carboxaldehyde and each of the following acid catalysts at 0.04%, 0.10%, 0.43% in DPM, 1.02% in DPM, and 2.04% in DPM: phenol, mesitylenic acid, caprylic acid, succinic acid, pivalic acid, tiglic acid, and benzoic acid.

FIG. 1 demonstrates that low vapor pressure acid catalysts provide up to 3 times better reduction of sulfur-based malodors in comparison to the control.

Analytical Test—Effect of Volatile Aldehydes and Acid Catalyst on Amine-Based and Sulfur-Based Malodors The above analytical test is repeated using sample formulations containing volatile aldehydes (or RA) and an acid catalyst, as outlined in Tables 8 and 9.

Tables 8 and 9 show that a perfume mixture having as little as 1% volatile aldehyde along with 1.5% acid catalyst performs better at reducing butylamine and butanethiol than the same perfume mixture having 5% volatile aldehyde.

TABLE 8

| Formulation | % butylamine reduction at 40 secs. | | % butanethiol reduction at 30 mins. | |
|---|---|---|---|---|
| Perfume Mixture w/5% RA (Control) | 34.21 | — | 2.40 | — |
| Perfume Mixture w/1% RA and w/ 1.5% Benzoic Acid | 41.63 | +7.42 | 11.95 | +9.55 |
| Perfume Mixture w/3% RA and w/ 1.5% Benzoic Acid | 36.19 | +1.98 | 13.56 | +11.16 |
| Perfume A Mixture w/5% RA and w/ 1.5% Benzoic Acid | 41.26 | +7.05 | 9.56 | +5.02 |

TABLE 9

| Formulation | % butylamine Reduction at 40 secs. | | % butanethiol reduction at 30 mins. | |
|---|---|---|---|---|
| Perfume mixture w/5% RA (Control) | 4.94 | — | 10.52 | — |
| Perfume mixture w/1% RA and w/ 1.5% Benzoic Acid | 11.61 | +6.67 | 18.82 | +8.30 |
| Perfume mixture w/3% RA and w/ 1.5% Benzoic Acid | 26.89 | +21.95 | 14.85 | +4.33 |
| Perfume mixture w/5% RA and w/ 1.5% Benzoic Acid | 20.27 | +15.33 | 16.84 | +6.32 |

Sensory Test—Effect of Volatile Aldehydes on a Sulfur-Based Malodor

Place Presto™ skillet into fume hood and turn on to 250° F. Place 80 grams of Crisco® oil into skillet and cover with skillet lid. Allow 10 minutes for equilibration. Remove skillet lid and check oil temperature with thermometer. Place 50 grams of chopped, commercially prepared garlic in water into skillet. Cover skillet with lid. Cook for 2.5 minutes or until garlic is translucent, with a portion staring to turn brown but not burn. Remove garlic from the skillet. Place 5 grams of garlic in each of 4 Petri dishes. Place covers on each Petri dish.

Place each covered Petri dish into individual test chambers. Each test chamber is 39.25 inches wide, by 25 inches deep, by 21.5 inches high with a volume of 12.2 cubic feet (0.34 cubic meters). The test chamber can be purchased from Electro-Tech Systems, Glenside, Pa. Each test chamber is equipped with a fan (Newark catalog #70K9932, 115 VAC, 90CFM) purchased from Newark Electronics, Chicago, Ill.

Remove the lids of the Petri dishes to expose the malodor for a dwell time sufficient to provide an initial odor intensity grade of 70-80 (about 1 minute). Once the initial odor intensity grade has been reached in a test chamber, remove the Petri dish from the test chamber.

Next, 3 Febreze® Noticeables™ air freshening devices, marketed by The Procter and Gamble Company, are each filled with the Control composition shown in Table 10.

TABLE 10

Control Composition

| Material Name | Wt % |
| --- | --- |
| Benzaldehyde | 0.150 |
| Floralozone | 0.097 |
| Helional | 1.455 |
| Hydroxycitronellal | 3.880 |
| Ligustral Or Triplal | 1.028 |
| Esters | 12.950 |
| Ethers | 50.190 |
| Ketones | 3.010 |
| Lactones | 0.490 |
| Alcohols | 21.610 |
| Terpenes | 5.140 |

The devices are set to the low intensity position and plugged into 3 of the 4 test chambers. All doors on chamber are closed.

At 5, 15, 20, 30, 45, and 60 minutes, trained evaluators open each chamber, smell the chamber for malodor intensity, and assign a malodor score, based on the scale in Table 11. The chamber door is closed but not locked between sequential evaluators. The scores are tabulated and the average score for each time interval is recorded.

TABLE 11

Expert Sensory Grader Malodor Evaluation Scale

| Score | Description corresponding to Score |
| --- | --- |
| 0 | No malodor present |
| 10 | Very slight malodor - "I think there is a malodor present." |
| 20 | Slight malodor - "I detect something but cannot identify specific malodor." |
| 25 | Slight malodor |
| 50 | Moderate |
| 75 | Strong Malodor |
| 100 | Extremely Strong Malodor |

The above protocol is repeated using Prototype 1 shown in Table 12 (instead of Control composition in Table 10).

TABLE 12

Prototype 1

| Material Name | Wt. % |
| --- | --- |
| Benzaldehyde | 0.135 |
| Floralozone | 0.087 |
| Helional | 1.310 |
| Hydroxycitronellal | 3.492 |
| Ligustral Or Triplal | 0.925 |
| o-anisaldehyde | 2.500 |
| Intreleven Aldehyde | 0.500 |
| Florhydral | 1.000 |
| Floral Super | 2.500 |
| Scentenal | 1.000 |
| Cymal | 2.500 |
| esters | 11.662 |
| ethers | 45.171 |
| ketones | 2.705 |
| lactones | 0.437 |
| alcohols | 19.446 |
| terpenes | 4.632 |

The above protocol is repeated using Prototype 2 shown in Table 13.

TABLE 13

Protoype 2

| Material Name | Wt. % |
| --- | --- |
| Benzaldehyde | 0.135 |
| Floralozone | 0.087 |
| Helional | 1.310 |
| Hydroxycitronellal | 3.492 |
| Ligustral Or Triplal | 0.925 |
| o-anisaldehyde | 2.250 |
| Intreleven Aldehyde | 0.450 |
| Florhydral | 0.900 |
| Floral Super | 2.250 |
| Scentenal | 0.900 |
| Cymal | 2.250 |
| 5-Methyl Thiophene Carboxaldehyde | 1.000 |
| Esters | 11.662 |
| Ethers | 45.171 |
| Ketones | 2.705 |
| Lactones | 0.437 |
| Alcohols | 19.446 |
| Terpenes | 4.632 |

Figure 2:
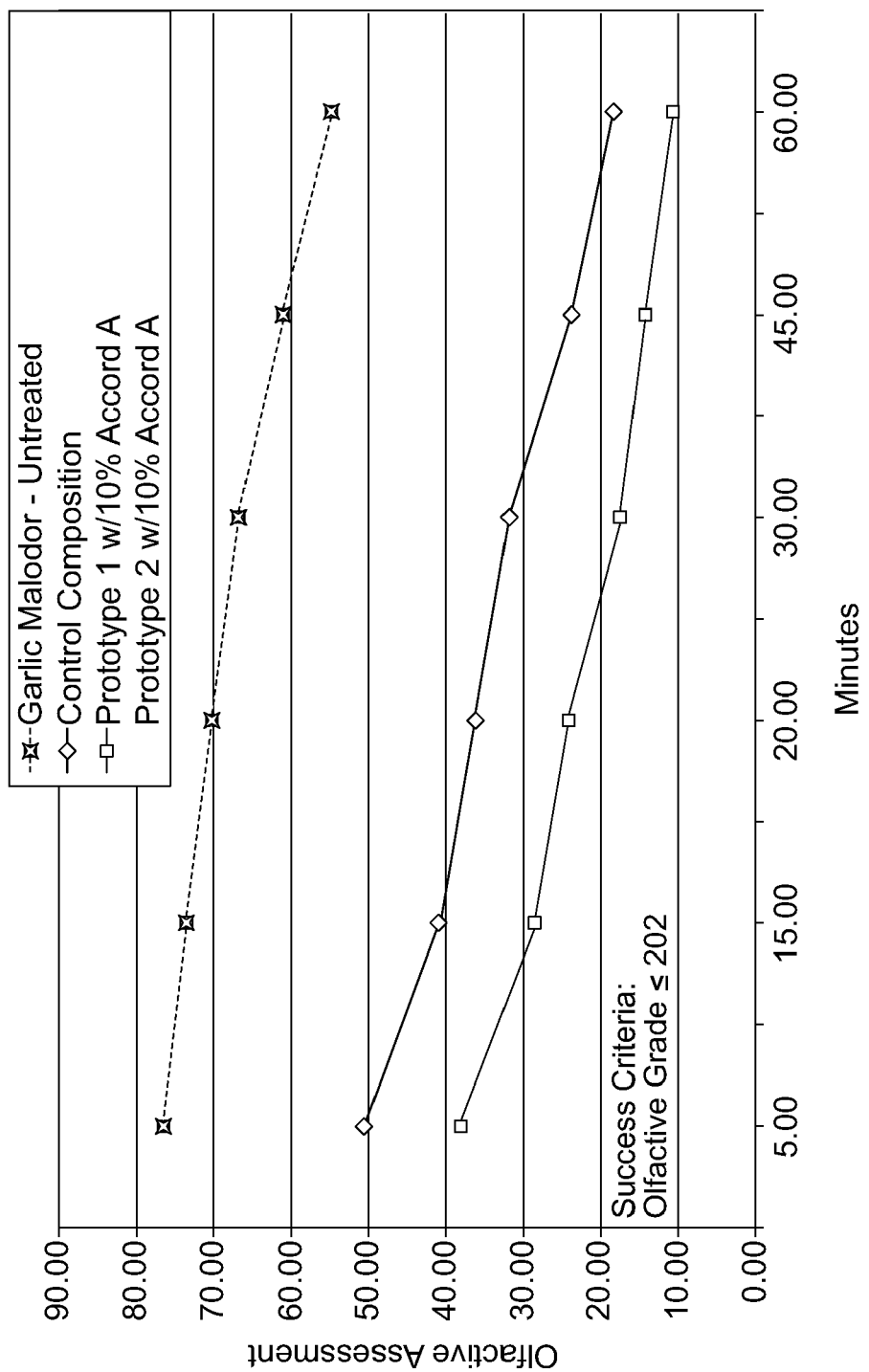
FIG. 2 is a graph showing the performance of one embodiment of a malodor control composition, in accordance with the present invention, on a sulfur-based malodor.

FIG. 2 shows that the formulation having 10% of the malodor control composition of the present invention reduces the garlic malodor more than the Control composition that lacks such malodor control composition.

Sensory Test—Effect of Volatile Aldehydes on an Amine-Based Malodor

Separate fresh ocean perch fillets from skin and add to a Magic Bullet™ food chopper. Fish meat is chopped for 35-40 seconds. 25 grams of chopped fish is weighed and fashioned into a patty suitable to fit into a 60×15 mm Petri dish. Repeat 3 more times so there is one fish patty in each of 4 Petri dishes. Add 40 g of Crisco® oil to Presto™ skillet. Place lid on skillet and turn on to 350° F. Allow 10 minutes for equilibration. Remove lid. Cut a slit in the middle of each patty, place 1 patty into skillet, and begin frying. Replace lid. After 2.5 minutes, flip fish patty and fry an additional 2.5 minutes. Remove fish patty from skillet and blot briefly onto a paper towel for 10 seconds. Fry the remaining 3 patties in the same manner. Place each fish patty into a 60×15 mm Petri dish and cover with a lid.

Introduce each Petri dish containing a fish patty into individual test chambers. The specifications of the test chamber are the same as those in the above sulfur-based (i.e. garlic)

malodor test. Remove the lids to expose the malodor for a dwell time sufficient for providing an initial odor intensity grade of 70-80 (about 1 minute). Once the initial odor intensity grade has been reached in a test chamber, remove the Petri dish from the test chamber.

Next, 3 Febreze Noticeables air freshening devices, marketed by The Procter and Gamble Company, are each filled with the Control composition outlined in Table 10. The devices are set to the low intensity position and plugged into 3 of the 4 test chambers. All doors on chamber are closed.

At 5, 15, 20, 30, 45, and 60 minutes, trained evaluators open each chamber, smell the chamber for malodor intensity, and assign a malodor score, based on the scale in Table 9. The chamber door is closed but not locked between sequential evaluators. The scores are tabulated and the average score for each time interval is recorded.

The above protocol is repeated using Prototype 1 shown in Table 12 (instead of Control composition); and then using Prototype 2 shown in Table 13.

Figure 3:
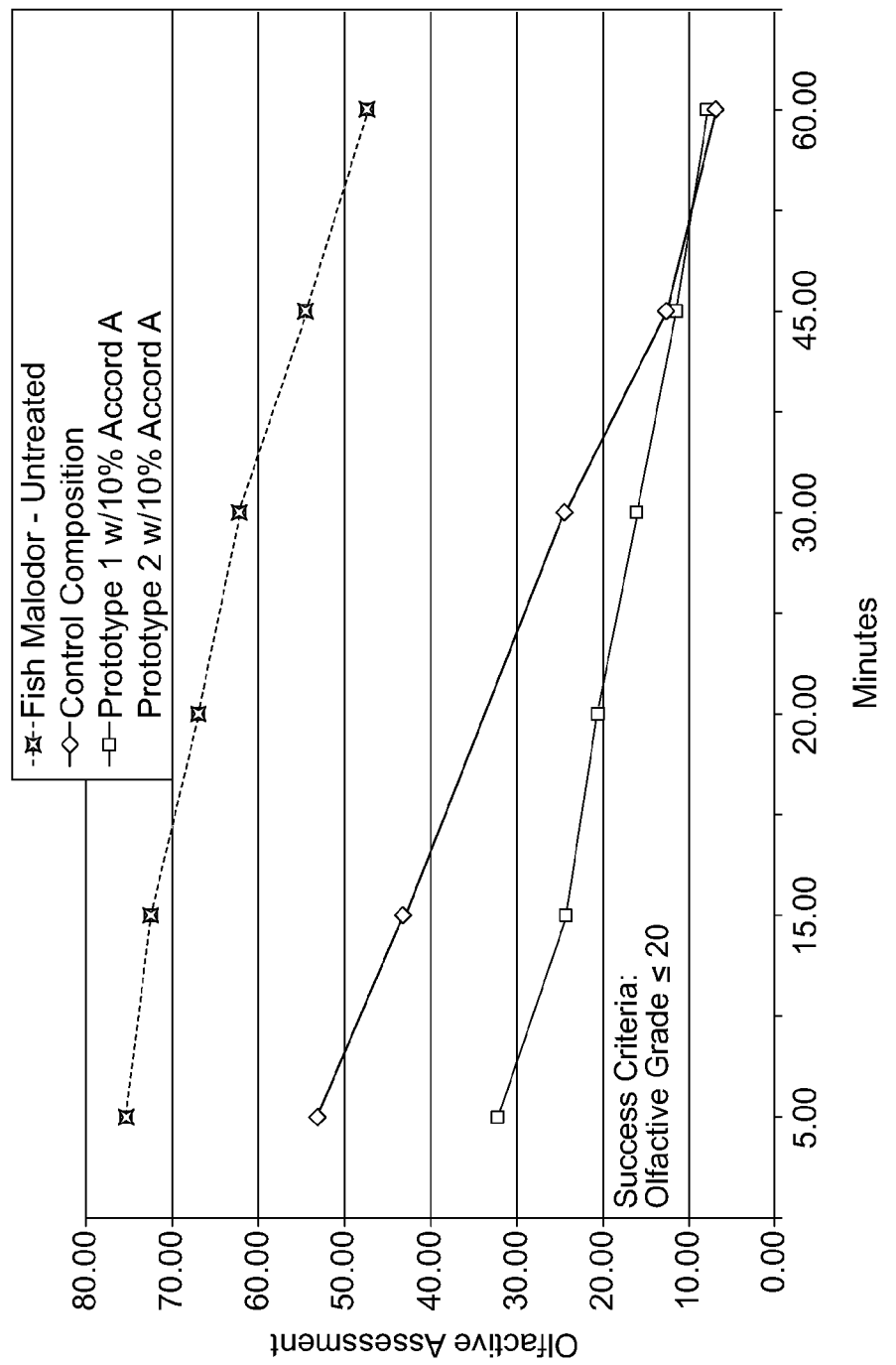
FIG. 3 is a graph showing the performance of one embodiment of a malodor control composition, in accordance with the present invention, on an amine-based malodor.

FIG. 3 shows that the formulation having 10% of the malodor control composition of the present invention reduces the fish malodor more than the Control that lacks such malodor control composition.

Sensory Test—Effect of Volatile Aldehyde and Acid Catalyst on an Amine-Based and Sulfur-Based Malodors The above sensory test protocols for amine-based and sulfur-based malodors are repeated using the 2 formulations outlined in Table 14; and then using the 2 formulations outlined in Table 15, except the Table 15 formulations are separately loaded into 2 Febreze® Set & Refresh passive air fresheners, marketed by The Procter and Gamble Company (vs. Febreze Noticeables devices). Results are shown in Tables 14 and 15.

Tables 14 and 15 demonstrates that perfume formulations with 1% volatile aldehyde and 1.5% acid catalyst provide malodor removal benefit equal to or better than perfume formulations with 5% volatile aldehyde alone.

TABLE 14

Sensory testing for malodor reduction with Febreze Noticeables air (10 replicates per test):

| Formulation | Amine - Fish Malodor Removal | | Thiol - Garlic Malodor Removal | |
| --- | --- | --- | --- | --- |
| Perfume mixture w/5% RA (Control) | *20 mins. | — | *22 mins. | — |
| Perfume mixture w/1% RA and w/1.5% benzoic acid | *16 mins. | +4 | *20 mins. | +2 |

*Meets Success Criteria: Olfactive Grade <20 at defined time.

TABLE 15

Sensory testing for malodor reduction with Febreze Set & Refresh (10 replicates per test):

| Formulation | Amine - Fish Malodor Removal | |
| --- | --- | --- |
| Perfume mixture w/5% RA (Control) | *23 mins. | — |
| Perfume mixture w/1% RA and w/1.5% benzoic acid | *12 mins. | +11 |

*Meets Success Criteria: Olfactive Grade <20 at defined time.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:

1. A malodor control composition comprising: at least one volatile aldehyde; and an acid catalyst consisting of 5-methyl thiophene carboxylic acid.

2. The malodor control composition of claim 1 wherein said at least one volatile aldehyde has a VP of about 0.001 torr to about 50 torr.

3. The malodor control composition of claim 1 wherein said at least one volatile aldehyde has a VP of about 0.001 torr to about 15 torr.

4. The malodor control composition of claim 1 wherein said at least one volatile aldehyde is selected from the group consisting of 2-ethoxy benzylaldehyde, 2-isopropyl-5-methyl-2-hexenal, 5-methyl furfural, 5-methyl-thiophene-carboxaldehyde, adoxal, p-anisaldehyde, benzylaldehyde, bourgenal, cinnamic aldehyde, cymal, decyl aldehyde, 4,8-dimethyl-4,9-decadienal, florhydral, helional, lauric aldehyde, ligustral, lyral, melonal, o-anisaldehyde, pino acetaldehyde, P.T. bucinal, thiophene carboxaldehyde, trans-4-decenal, trans, trans-2,4-nonadienal, undecyl aldehyde, and mixtures thereof.

5. The malodor control composition of claim 1 wherein said at least one volatile aldehyde is selected from the group consisting of 4,8-dimethyl-4,9-decadienal, o-anisaldehyde, and mixtures thereof.

6. The malodor control composition of claim 1 wherein said at least one volatile aldehydes is present in an amount from about 1% to about 10%, by weight of said malodor control composition.

7. The malodor control composition of claim 1 wherein said at least one volatile aldehyde is present in an amount from about 1% to about 5%, by weight of said malodor control composition, and said acid catalyst is present in an amount of about 0.4% to about 1.5%, by weight of said malodor control composition.

8. The malodor control composition of claim 1 wherein said at least one volatile aldehyde comprises a mixture of volatile aldehydes selected from the group consisting of Accord A, Accord B, Accord C, and mixtures thereof.

9. The malodor control composition of claim 1 wherein said at least one volatile aldehyde comprises a mixture of volatile aldehydes, said mixture comprising about 1% to about 10% of Accord A, by weight of said malodor control composition.

10. The malodor control composition of claim 1 wherein said acid catalyst is present in an amount from about 0.1% to about 0.4%, by weight of said malodor control composition.

11. The malodor control composition of claim 1 wherein said acid catalyst is present in an amount of about 0.4%, by weight of said malodor control composition.

12. The malodor control composition of claim 1 wherein said composition has a pH of about 4 to about 6.5.

13. The malodor control composition of claim 1 further comprising an ingredient selected from the group consisting of: odor masking agents, odor blocking agents, diluents, and mixtures thereof.

14. A method of neutralizing malodor comprising contacting said malodor with the malodor control composition of claim 1.

* * * * *